(12) United States Patent
Carlson et al.

(10) Patent No.: US 11,033,296 B2
(45) Date of Patent: Jun. 15, 2021

(54) SYSTEMS AND METHODS FOR DYNAMIC TRAJECTORY CONTROL

(71) Applicant: Intuitive Surgical Operations, Inc., Sunnyvale, CA (US)

(72) Inventors: Christopher R. Carlson, Belmont, CA (US); Randall L. Schlesinger, San Mateo, CA (US); Federico Barbagli, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 983 days.

(21) Appl. No.: 15/505,855

(22) PCT Filed: Aug. 20, 2015

(86) PCT No.: PCT/US2015/046084
§ 371 (c)(1),
(2) Date: Feb. 22, 2017

(87) PCT Pub. No.: WO2016/032848
PCT Pub. Date: Mar. 3, 2016

(65) Prior Publication Data
US 2017/0273712 A1    Sep. 28, 2017

Related U.S. Application Data

(60) Provisional application No. 62/041,038, filed on Aug. 23, 2014.

(51) Int. Cl.
*A61B 17/34* (2006.01)
*A61B 5/06* (2006.01)
(Continued)

(52) U.S. Cl.
CPC .......... *A61B 17/3403* (2013.01); *A61B 5/061* (2013.01); *A61B 5/062* (2013.01);
(Continued)

(58) Field of Classification Search
None
See application file for complete search history.

(56) References Cited

U.S. PATENT DOCUMENTS 5,284,156 A * 2/1994 Schramm .......... A61B 10/0275
600/567
5,415,169 A * 5/1995 Siczek ................ A61B 6/0435
600/427

(Continued)

FOREIGN PATENT DOCUMENTS

CN    1850008 A    10/2006
EP    1103223 A2    5/2001
(Continued)

OTHER PUBLICATIONS

International Preliminary Report on Patentability for Application No. PCT/US2015/046084, dated Mar. 9, 2017, 10 pages.

(Continued)

*Primary Examiner* — Kaylee R Wilson
*Assistant Examiner* — Jay B Shah
(74) *Attorney, Agent, or Firm* — Haynes and Boone, LLP

(57) ABSTRACT

A biopsy system includes a biopsy tool and a control system in communication with the biopsy tool. The control system is configured to receive a command to perform a biopsy, retrieve a predefined dynamic trajectory for performing the biopsy from a memory device, and control the biopsy tool to move according to the predefined dynamic trajectory to perform the biopsy. The predefined dynamic trajectory includes a plurality of dynamic control modes. Each of the plurality of dynamic control modes has a different displace- (Continued)

ment profile. At least one different displacement profile comprises a cyclic displacement profile.

21 Claims, 9 Drawing Sheets

(51) Int. Cl.
    *A61B 5/053*     (2006.01)
    *A61B 10/02*     (2006.01)
    *A61B 10/04*     (2006.01)
    *A61B 34/30*     (2016.01)
    *A61B 90/00*     (2016.01)
    *A61B 5/0538*     (2021.01)
    *A61B 10/06*     (2006.01)

(52) U.S. Cl.
    CPC .......... *A61B 10/0283* (2013.01); *A61B 10/04* (2013.01); *A61B 5/0538* (2013.01); *A61B 10/06* (2013.01); *A61B 2010/045* (2013.01); *A61B 2017/3405* (2013.01); *A61B 2034/301* (2016.02); *A61B 2090/064* (2016.02)

(56) References Cited

U.S. PATENT DOCUMENTS

| | | | |
|---|---|---|---|
| 6,380,732 B1 | 4/2002 | Gilboa | |
| 6,389,187 B1 | 5/2002 | Greenaway et al. | |
| 7,316,681 B2 | 1/2008 | Madhani | |
| 7,772,541 B2 | 8/2010 | Froggatt et al. | |
| 8,900,131 B2 | 12/2014 | Chopra et al. | |
| 9,259,274 B2 | 2/2016 | Prisco | |
| 9,452,276 B2 | 9/2016 | Duindam et al. | |
| 2003/0199898 A1 | 10/2003 | Boecker et al. | |
| 2004/0082915 A1 | 4/2004 | Kadan | |
| 2006/0013523 A1 | 1/2006 | Childers et al. | |
| 2006/0149147 A1 | 7/2006 | Yanof et al. | |
| 2007/0016067 A1* | 1/2007 | Webster, III | A61B 90/10 600/464 |
| 2011/0015649 A1* | 1/2011 | Anvari | A61B 34/20 606/130 |
| 2011/0213270 A1* | 9/2011 | Pison | A61B 10/02 600/562 |
| 2012/0109335 A1* | 5/2012 | May | A61F 2/4657 623/23.72 |
| 2012/0265051 A1* | 10/2012 | Fischer | A61B 34/76 600/411 |
| 2012/0289777 A1* | 11/2012 | Chopra | A61B 5/02028 600/109 |
| 2013/0102886 A1* | 4/2013 | Mark | A61B 1/32 600/424 |
| 2013/0296737 A1 | 11/2013 | McMillan et al. | |
| 2015/0297864 A1* | 10/2015 | Kokish | A61B 34/30 604/95.04 |

FOREIGN PATENT DOCUMENTS

| | | |
|---|---|---|
| WO | WO-0028882 A2 | 5/2000 |
| WO | WO-2007030173 A1 | 3/2007 |
| WO | WO-2007141784 A2 | 12/2007 |
| WO | WO-2009156397 A1 | 12/2009 |
| WO | WO-2011057260 A2 | 5/2011 |
| WO | WO-2012158324 A2 | 11/2012 |
| WO | WO-2013013142 A1 | 1/2013 |

OTHER PUBLICATIONS

International Search Report and Written Opinion for Application No. PCT/US2015/046084, datedDec. 21, 2015, 14 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP15836579.1, dated Feb. 19, 2018, 10 pages.

* cited by examiner

SYSTEMS AND METHODS FOR DYNAMIC TRAJECTORY CONTROL

RELATED APPLICATIONS

This patent application is the U.S. National Phase of International Application No. PCT/US2015/046084, filed Aug. 20, 2015, which designated the U.S. and claims priority to and the benefit of the filing date of U.S. Provisional Patent Application 62/041,038, entitled "SYSTEMS AND METHODS FOR DYNAMIC TRAJECTORY CONTROL," filed Aug. 23, 2014, which is incorporated by reference herein in its entirety.

FIELD

The present disclosure is directed to systems and methods for performing surgical procedures, and more particularly, to systems and methods for controlling motion of a medical instrument within a patient's anatomy.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Clinicians may insert medical tools through these natural orifices or incisions to reach a target tissue location. Medical tools include instruments such as therapeutic instruments, diagnostic instruments, and surgical instruments. To reach the target tissue location, a minimally invasive medical tool may navigate natural or surgically created passageways in anatomical systems such as the lungs, the colon, the intestines, the kidneys, the heart, the circulatory system, or the like. One example of a medical tool is a biopsy instrument.

Some medical instruments, such as biopsy instruments, may be controlled through use of a user input mechanism from a user control station. Specifically, certain motions of the user input mechanism cause corresponding movements of the medical instrument. The effectiveness of some medical procedures is strongly correlated with dynamic characteristics of the medical instrument during the procedure. For example, dynamic characteristics of the biopsy needle during a biopsy procedure will affect the usefulness of samples obtained from the biopsy.

SUMMARY

The embodiments of the invention are summarized by the claims that follow below.

In one example, a method for performing a medical procedure includes receiving a command to initiate tissue sampling with a surgical instrument at a target location, retrieving a predefined dynamic trajectory for tissue sampling from a memory device, and moving the surgical instrument according to the predefined dynamic trajectory to sample tissue at the target location.

In one example, a biopsy system includes a biopsy tool, and a control system in communication with the biopsy tool, the control system configured to receive a command to perform a biopsy, retrieve a predefined dynamic trajectory for performing the biopsy from a memory device, and control the biopsy tool to move according to the predefined dynamic trajectory to perform the biopsy.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1:
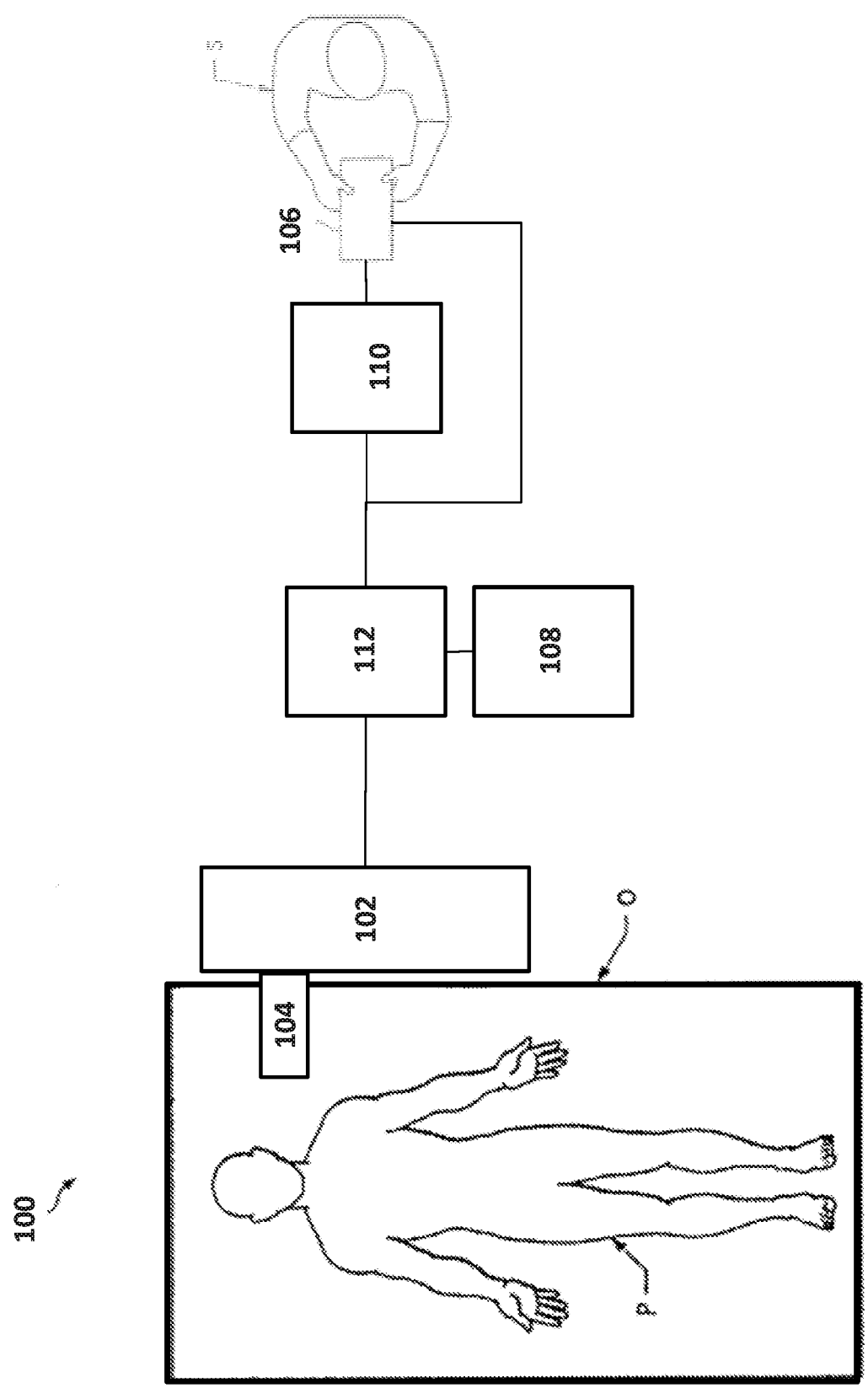
FIG. 1 is a diagram showing an illustrative teleoperational medical system, according to one example of principles described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1 of the drawings, a teleoperational medical system for use in, for example, medical procedures including diagnostic, therapeutic, or surgical procedures, is generally indicated by the reference numeral 100. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures.

As shown in FIG. 1, the teleoperational system 100 generally includes a teleoperational assembly 102 for operating a medical instrument system 104 in performing various procedures on the patient P. The movement of the medical instrument is performed in an anatomical frame of reference $X_A$, $Y_A$, $Z_A$. The assembly 102 is mounted to or near an operating table O on which a patient P is positioned. The medical instrument system 104 is operably coupled to the teleoperational assembly 102. An operator input system 106 allows a surgeon or other type of clinician S to view images of or representing the surgical site and to control the operation of the medical instrument system 104.

In alternative embodiments, the teleoperational system may include more than one manipulator assembly. The exact number of manipulator assemblies will depend on the surgical procedure and the space constraints within the operating room among other factors.

The operator input system 106 may be located at a surgeon's console, which is usually located in the same room as operating table O. However, it should be understood that the surgeon S can be located in a different room or a completely different building from the patient P. Operator input system 106 generally includes one or more control device(s) for controlling the medical instrument system 104. The movement of the control devices are tracked in an operator frame of reference $X_O$, $Y_O$, $Z_O$. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2) may include a viewing scope assembly (described in greater detail below) such that a concurrent or real-time image of the surgical site is provided to surgeon console. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below).

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

The display system 110 may also display an image of the surgical site and medical instruments captured by the visualization system. The display 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 110 may present images of the surgical site recorded and/or modeled preoperatively using imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The presented preoperative images may include two-dimensional, three-dimensional, or four-dimensional images. The presented preoperative or intra-operative images may include two-dimensional, three-dimensional, or four-dimensional (including e.g., time based or velocity based information) images and associated image data sets for reproducing the images.

In some embodiments, the display 110 may display a virtual navigational image in which the actual location of the medical instrument 104 is registered (i.e., dynamically referenced) with preoperative or concurrent images to present the surgeon S with a virtual image of the internal surgical site at the location of the tip of the instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display 110 may display a virtual navigational image in which the actual location of the medical instrument is registered with preoperative or concurrent images to present the surgeon S with a virtual image of medical instrument within the surgical site from an external or internal viewpoint. An image of a portion of the medical instrument or other graphical or alphanumeric indicators may be superimposed on the virtual image to assist the surgeon controlling the instrument 104.

The teleoperational medical system 100 also includes a control system 112. The control system 112 includes at least one memory and at least one processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104. Virtual navigation using the virtual visualization system is based upon reference to an acquired dataset associated with the three dimensional structure of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intraoperatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 2:
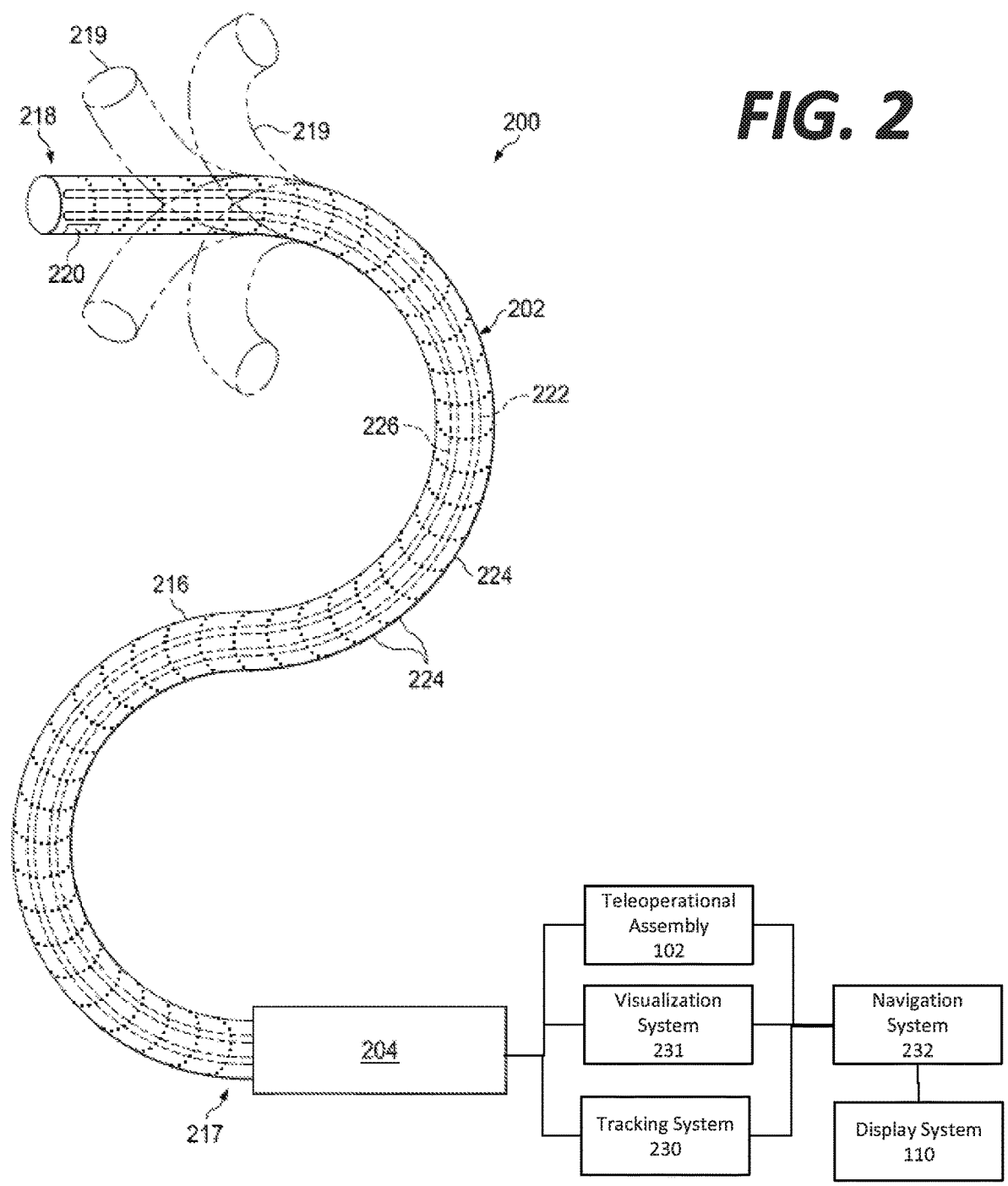
FIG. 2 is a diagram showing an illustrative medical instrument system comprising an endoscopic visualization system, according to one example of principles described herein.

FIG. 2 illustrates a medical instrument system 200, which may be used as the medical instrument system 104 of teleoperational medical system 100. Alternatively, the medical instrument system 200 may be used for non-teleoperational exploratory procedures or in procedures involving traditional manually operated medical instruments, such as endoscopy.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller.

The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. The optical fiber may be used to monitor the shape of at least a portion of the catheter system 202. More specifically, light passing through the optical fiber is processed to detect the shape of the catheter system 202 and to utilize that information to assist in surgical procedures. The sensor system (e.g., sensor system 108) may include an interrogation system for generating and detecting the light used for determining the shape of the catheter system 202. This information, in turn, can be used to determine other related variables, such as velocity and acceleration of the parts of a medical instrument system. The sensing may be limited only to the degrees of freedom that are actuated by the teleoperational system, or it may be applied to both passive (e.g., unactuated bending of the rigid members between joints) and active (e.g., actuated movement of the instrument) degrees of freedom.

In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument system during a procedure may be used to represent the shape of the instrument, particularly if an anatomical passageway is generally static. Alternatively, a wireless device with position or orientation controlled by an external magnetic field may be used for shape sensing. The history of the wireless device's position may be used to determine a shape for the navigated passageways.

The medical instrument system may optionally include a position sensor system 220. The position sensor system 220 may be a component of an EM sensor system with the sensor 220 including one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

A tracking system 230 may include the position sensor system 220 and a shape sensor system 222 for determining the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of a control system 116.

The flexible catheter body 216 includes a channel sized and shaped to receive an auxiliary instrument 226. Auxiliary instruments may include, for example, image capture probes, biopsy instruments, laser ablation fibers, or other surgical, diagnostic, or therapeutic tools. Auxiliary tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the auxiliary tool 226 may be an image capture probe that includes a distal portion with a stereoscopic or monoscopic camera at or near the distal end 218 of the flexible catheter body 216 for capturing images (including video images) that are processed by a visualization system 231 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

The auxiliary instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomical systems, including the colon, the intestines, the kidneys, the brain, the heart, the circulatory system, and the like.

The information from the tracking system 230 may be sent to a navigation system 232 where it is combined with information from the visualization system 231 and/or the preoperatively obtained models to provide the surgeon or other operator with real-time position information on the display system 110 for use in the control of the instrument 200. The control system 116 may utilize the position information as feedback for positioning the instrument 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety.

In the embodiment of FIG. 2, the instrument 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

To perform certain types of surgical procedures, a medical instrument (e.g., instrument 200 with catheter body 216) is inserted into a patient. As described above, the catheter body 216 includes a channel sized and shaped to receive an auxiliary instrument 226 such as a biopsy tool. Optionally, the biopsy tool may be a nested biopsy tool including a cannulated biopsy needle with an obturator extending within the needle. The catheter may navigate various anatomical passageways to arrive at a catheter park location. The catheter park location is the location from which the surgical procedure, such as the biopsy, is to be performed. In the example of a biopsy surgical procedure, the biopsy tool can be controlled remotely by a surgeon. Specifically, the surgeon may manipulate various control devices to cause specific movement of a biopsy tool with respect to the catheter in order to perform the biopsy procedure. Particularly, the tip of the biopsy tool includes a needle that is extendable from the catheter as the biopsy tool moves with respect to the catheter. With traditional, fully manual procedures, the effectiveness of a biopsy procedure (including fine needle aspiration procedures) is dependent upon the skill of the clinician performing the procedure. With fully manual procedures, the clinician controls various aspects of the motion of the biopsy instrument including position, orientation, velocity, acceleration, and reciprocation patterns. As will be described below, all or portions of the clinician controlled motion of the biopsy instrument may be modified, augmented, or replaced with predefined dynamic routines.

According to principles described herein, movement of a surgical tool, such as a biopsy instrument, is controlled with a predefined dynamic trajectory. The predefined dynamic trajectory may be based, for example, on a pre-programmed dynamic trajectory model or output that may be optimized for the current patient conditions or a recorded trajectory resulting from prior manual input by a skilled surgeon. For example, in the case of a biopsy procedure, the dynamic trajectory of the biopsy needle as it enters the target tissue and extracts samples of tissue can be recorded when a skilled surgeon performs the operation. The recorded trajectory can then be used as a predefined trajectory that is used to move the biopsy needle in subsequent biopsy procedures regardless.

Figure 3:
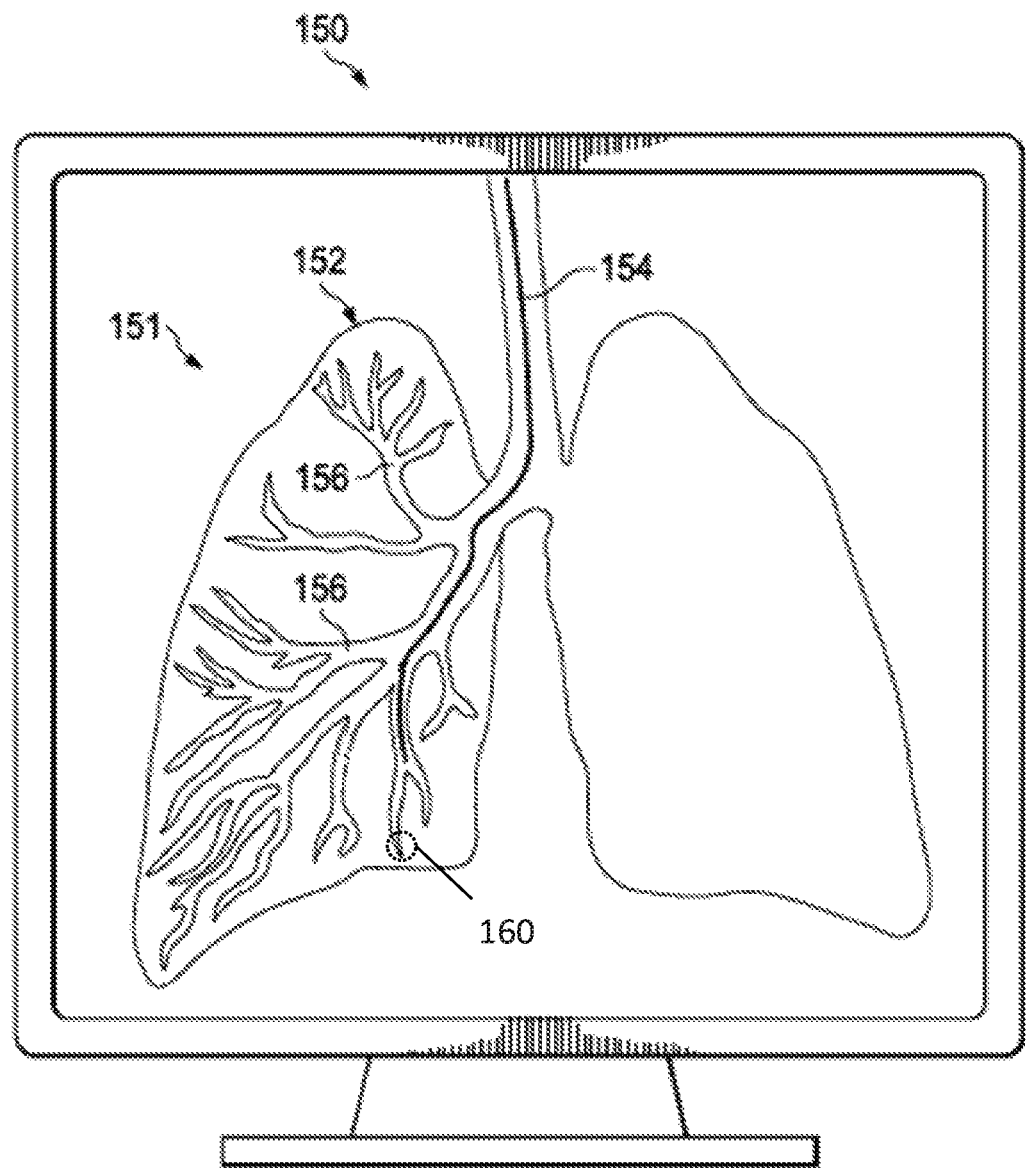
FIG. 3 is a diagram showing a model patient anatomy and a target location, according to one example of principles described herein.

FIG. 3 depicts a composite image 150 including a model 151 of a human lung 152, from a viewpoint external to the lung. Such an image shows an illustrative path to a target location. At the target location, a biopsy procedure can be performed according to principles described herein. The model lung 151 is registered with an instrument image 154 of a flexible instrument, such as catheter system 202. The model 151 of the lung 152 may be generated from a set of scanned images (e.g., pre-operative CT or MRI images) using a modeling function such as a segmentation process. The composite image 150 may be displayed via display system 110. As the instrument is advanced through bronchial passageways 156 of the lung 152, information from the tracking system 230 and/or the visualization system 231 is used to register the instrument image 154 with the model lung image 151. The view of the model 151 of the lung 152 may change, for example, to depict the lung in a state of inspiration or expiration. The instrument image 154 may change to depict the advancement or withdrawal of the instrument through the bronchial passageways 156. In some examples, the model 151 may also include a target region 160. The target region 160 may represent a destination for the surgical instrument. For example, when performing a biopsy, the tissue to be extracted is within the target region 160. Thus, the surgeon can use the model 151 to plan a route for the instrument to reach the target region 160.

Figure 4:
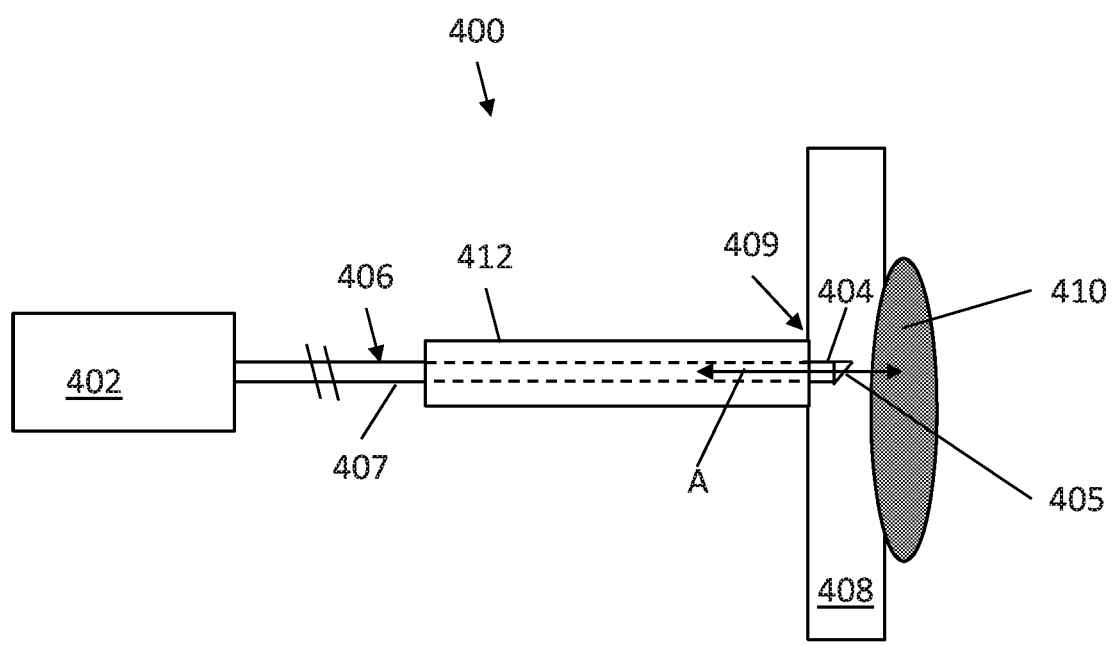
FIG. 4 is a diagram showing an illustrative catheter that is positioned at a target location, according to one example of principles described herein.

FIG. 4 is a diagram showing an illustrative medical instrument system 400 (e.g., system 200) that includes a catheter 412 through which an auxiliary instrument such as a biopsy instrument 406 extends. The biopsy instrument 406 includes an elongated body 407 with a biopsy needle tip 404 at a distal end of the elongated body. The catheter 412 includes a working channel that is sized and shaped to receive the instrument 400. The biopsy instrument 406 is coupled to a biopsy instrument carriage 402. The catheter 412 is inserted into a patient and navigated through anatomic passageways to a park location 409 along a wall 408 of the anatomic passageway. The biopsy instrument 406 is inserted into the working channel of the catheter 412 before, during, or after the catheter navigation. The biopsy instrument 406 can be extended from the catheter 412, through the wall 408, to perform a biopsy procedure on a target location 410.

The biopsy instrument carriage 402 is part of the actuation system for the biopsy instrument 406. Responsive to control signals from the control system (e.g. control system 112), the carriage operates the instrument 406 in one or more degrees of freedom, including translation in an extension/retraction direction and movement of a least the tip 404 in pitch, yaw, and/or roll. For example, the carriage 402 may be coupled to a teleoperational assembly and, responsive to electrical signals from the control system motors in the carriage or teleoperational assembly, may move the instrument 406 relative to catheter 412 according to a predefined trajectory. The movement of the catheter 412 and the biopsy instrument 406 can be independently controlled in multiple degrees of freedom, including translation along an axis, pitch, yaw, and roll. The trajectory may be defined by specific distances, velocities, and accelerations or decelerations along a timeline. More detail about trajectories will be described below.

The needle tip 404 is designed to pierce tissue and obtain samples for further study or analysis. In many cases, a target location 410 such as a suspected tumor is not within the walls of an anatomical passageway. Thus, the needle is used to pierce the walls of the passageway and extend deep enough to reach the suspected location. In some examples, however, the suspected location is within an anatomical passageway and thus the passageway wall 408 does not have to be pierced in order to obtain samples from the target location 410. The samples from the target location may be used for a variety of purposes such as a histological and/or cytological examination to determine whether the sampled tissue and cells are cancerous.

In some examples, the needle tip 404 is a rigid component that is fixed to the distal end of the flexible elongated body 406. The needle 404 may be one of many different shapes designed to cut and extract various types of tissue. In some examples, the needle may include movable parts designed to clip tissue for extraction. The term tissue as used herein may include individual cells, groups of cells, or larger sections of anatomical material. Various types of biopsy needles may be used in accordance with principles described herein.

The needle tip 404 includes a port 405 through which separated tissue may be collected for removal from target location 410. Tissue (including cell) samples may move into the port of the needle tip via a stabbing cutting action, a rotational cutting action, a scraping cutting action, the application of suction, or a combination of more than one collection process. The hollow needle tip 404 may be connected to an extraction lumen (not shown) within the body of the catheter 412. The extraction lumen may be connected to an external chamber that can be used to create a vacuum within the extraction lumen and thus the hollow needle tip 404. The vacuum provides a suction force that is used to extract tissue and cells that are cut free by movement of the needle. In some examples, an obturator (not shown) may be extended through the extraction lumen or hollow portion of the needle tip 404 when the suction force is not being used.

In some examples, the biopsy instrument 406 has an elongate shaft that transmits axial dynamics. For example, the elongated body 407 or needle tip 404 may include a coil. In some examples, the elongated body 406 or needle 404 may include a laser cut hypotube construction. The needle 404 may also include serrated edges or coarse surfaces that are optimized for scraping cells from the surrounding tissue structures rather than coring a tissue block from surrounding tissue.

According to certain illustrative examples, the biopsy needle can begin movement along a predefined dynamic trajectory in response to a user command. A user may engage a control device by tactile operation, voice command, eye-movement, or other user action to initiate the predefined dynamic trajectory. The predefined dynamic trajectory may include multiple dynamic control modes. For example, a predefined dynamic trajectory may include a dynamic control mode for performing an insertion phase of the biopsy procedure and another dynamic control mode for performing a sampling phase of the biopsy procedure. The insertion phase involves the needle, or tip of the instrument, being inserted into tissue a wall 408 of a passageway and through any intermediate tissue and then moved a distance such that the needle tip 404 is at the desired target location 410. Then a sampling phase is used to move the needle tip 404 in a reciprocating motion, along a longitudinal axis A through the needle tip 404 to perform the tissue collection. This second phase involves the actual cutting of tissue that is then extracted for analysis. For each phase, the dynamic trajectory may be predefined by a pre-programmed computer model or a recording of a manual input. In some cases, the insertion phase may be performed manually while the extraction phase is performed using a predefined dynamic trajectory.

Figure 5:
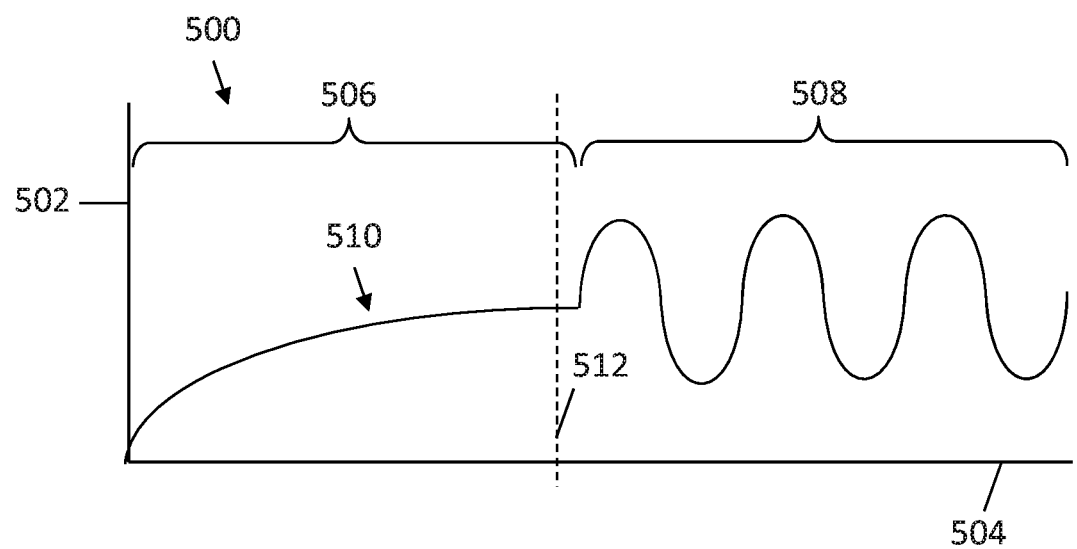
FIG. 5 is a diagram showing an illustrative predefined dynamic trajectory for a biopsy needle, according to one example of principles described herein.

FIG. 5 is a graph 500 showing a position component of an illustrative predefined dynamic trajectory 510 for a tool such as a biopsy instrument. According to the present example, the horizontal axis 504 represents time. The vertical axis 502 represents position of the biopsy instrument. Specifically, the vertical axis 502 represents the displacement (e.g., extension of the needle tip from the catheter or another initial position) of the biopsy instrument tip at a given point in time. The graph 500 illustrates two motion profiles representing two separate phases 506, 508 of a biopsy procedure. Motion profiles may represent, for example, position, velocity, or acceleration profiles for an instrument over a period of time. Particularly, the graph 500 illustrates position profiles representing an insertion phase 506 and a sampling phase 508.

The insertion phase 506 is the period during which the needle tip 404 travels from an initial position, such as a location at the entry of the catheter to an extraction position inside of or at the periphery of the target tissue 410. In the insertion phase, the biopsy needle will pass through some tissue that is generally not of interest before reaching the target tissue. This may be the case, for example, if a suspected tumor is underneath some healthy tissue. Thus, the needle has to pass through the healthy tissue before reaching the suspected tumor or adversely affected tissue. Dotted line 512 indicates the time at which the biopsy needle passes from the tissue that is not of interest to the target tissue. This time may be near or at the end of the insertion phase. The dynamics of the insertion phase 506 are intended to displace tissue in front of the needle without cutting cells or tissue samples from the surrounding tissue. In general the insertion phase 506 is a low dynamic phase. Specifically, the insertion phase involves lower velocities and lower rates of acceleration than are used in the tissue collection portion of the procedure. By inserting the biopsy needle into the tissue more carefully, damage to the patient's anatomy can be minimized.

The sampling phase 508 occurs after the biopsy needle tip has been inserted a desired displacement distance or to a desired depth. The sampling phase 508 involves a repetitive extension and retraction of the biopsy needle. Such reciprocal motion separates cells or larger tissue samples from the surrounding tissue for extraction. The sampling phase 508 may cut tissue and cells free from the surrounding tissue while minimizing the amount of bleeding. As compared to the insertion phase, the sampling phase generally involves a higher level dynamics Specifically, the sampling phase 508 may involve higher velocities and higher rates of acceleration. This quicker movement is used to effectively cut tissue and extract cells from the target location.

It is noted that the trajectory 510 illustrated in FIG. 5 represents motion in one translational degree of freedom, specifically, depth. Other aspects of the dynamic trajectory including movement in other degrees of freedom may be recorded and applied as described above. Such other trajectories may be used simultaneously. For example, while the biopsy needle is moving along the longitudinal axis as indicated in FIG. 5, the biopsy needle may be rotating around the longitudinal axis, pitching, yawing, or translating so as to perform the desired biopsy procedure. Each of the degrees of freedom may have a respective predefined dynamic trajectory. Additionally, the biopsy procedure may involve the movement of other components of the biopsy system. For example, the dynamic trajectory may indicate the time at which an obturator should be moved or removed so that a suction force is applied to the hollow needle. Specifically, the obturator may be engaged to block the extraction lumen or port or disengaged to open the extraction lumen or port.

The trajectory 510 illustrated in FIG. 5 indicates the position of the biopsy needle at a given point in time. Other dynamic characteristics, such as velocity and acceleration, of the dynamic trajectory during the insertion phase may be derived from the position of the biopsy needle. For example, the velocity of the biopsy needle at a given point in time is represented by the slope of the trajectory 510 at that point in time. Alternatively, the other predefined dynamic characteristics of the trajectory during the insertion phase may be represented by other graphs that illustrate velocity profiles or acceleration profiles as a function of time.

The predefined dynamic trajectory can be designed for a specific type of tissue. For example, some types of tissue are stiffer than others. Thus, the input signal used to cause the desired motion along the predefined dynamic trajectory may be different for different types of tissue impedance profiles. In some cases, different patient conditions may also affect the mechanical impedance of a particular type of tissue. The appropriate predefined dynamic trajectory can be selected by an operator based on such factors as the type of tissue or patient conditions. In some examples, the operator may select the appropriate predefined dynamic trajectory from a database. The database may be sorted according to target tissue types, patient condition, and other factors that may be relevant to motion of the biopsy tool during the biopsy procedure.

Figure 6:
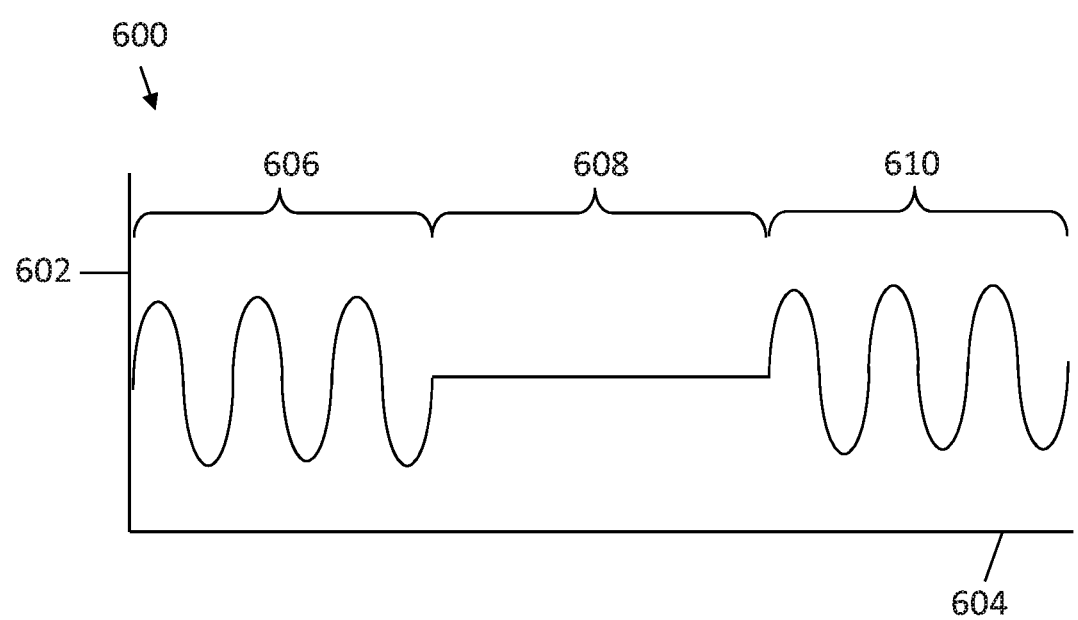
FIG. 6 is a diagram showing illustrative cycles within a predefined dynamic trajectory, according to one example of principles described herein.

As described above, the sampling phase involves repetitive insertion and extraction of the needle. Each insertion and sampling occurrence is referred to as a motion cycle. FIG. 6 is a graph showing illustrative motion cycles within a dynamic control mode of a predefined dynamic trajectory. According to the present example, the horizontal axis 604 represents time. The vertical axis 602 represents position. Specifically, the vertical axis 602 represents the displacement (e.g., extension of the needle tip from the catheter or another initial position) of the biopsy needle tip at a given point in time. The graph 600 illustrates position profiles representing different sub-phases of a sampling phase. Specifically, the graph 600 represents a first cutting phase 606, a first suction phase 608, a second cutting phase 610, and a second suction phase 612 of a sampling phase of a predefined dynamic trajectory.

The first cutting phase 606 includes a number of cycles of extensions and retractions. After the first cutting phase 606, a phase 608 may be a suction phase in which a suction system is activated to extract the cells that were cut free during the cutting phase 606. The suction system may be activated by the control system according to the predefined commands associated with the predefined dynamic trajectory. The suction phase may be considered part of the sampling dynamic control mode of the predetermined dynamic trajectory or may be considered a distinct suction control mode of the predefined dynamic trajectory. During the phase 608, the position of the biopsy needle tip remains relatively still. As described above, the biopsy needle tip includes a hollow center in fluid communication with a lumen of the catheter. A device in connection with the proximal end of the lumen can be used to create a vacuum within the lumen. This creates a suction force at the tip of the biopsy needle that will extract fluid, including the cells that were recently cut free into the needle and into the lumen. In general, the amount of material extracted during the biopsy may be minimized. In one example, the suction force is applied long enough to pull in approximately 10 centimeters of material. This means that the hollow portion of the needle, and possibly part of the lumen, will fill to a point approximately 10 centimeters from the tip of the needle. In some examples, a subsequent cutting phase 610 and suction phase 612 may be used to extract further material from the patient. The amount of suction provided for each suction phase 608, 610 can be such that the total amount of fluid and tissue that is extracted fills to a point approximately 10 centimeters from the tip of the biopsy needle. Other amounts of fluid can be extracted as well. For example, in some cases, 5, 15, or 20 centimeters of material may be extracted from the patient. In some examples, each cutting phase may involve a set number of motion cycles before the following suction phase occurs. Alternatively, the phase 608 may be an obturator removal phase in which an obturator, under separate actuation control from the biopsy instrument, is withdrawn from the biopsy instrument. The obturator removal phase may be considered part of the sampling dynamic control mode of the predetermined dynamic trajectory or may be considered a distinct suction control mode of the predefined dynamic trajectory.

In some examples, a high dynamic dither signal may be used to overlay the input signal used to cause the biopsy needle to move according to the predefined dynamic trajectory. The dither signal adds noise to the signal. Such noise may help the biopsy needle overcome frictional forces as it moves back and forth through the target tissue. In some examples, the dither signal may be modifiable by an operator. For example, the pulse shape, frequency, or amplitude of the dither signal may be modified as desired.

Figure 7:
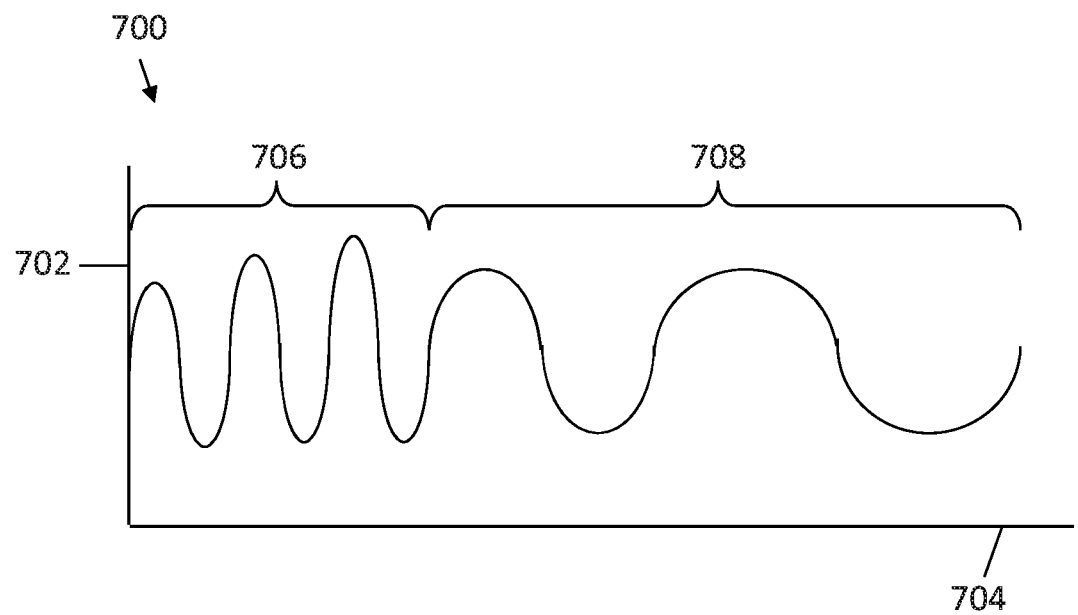
FIG. 7 is a diagram showing illustrative variation of cycles within a predefined dynamic trajectory, according to one example of principles described herein.

While FIG. 6 illustrates cycles that are similar to one another, other embodiments of predefined dynamic trajectories may include cycles that vary. FIG. 7 is a graph 700 showing illustrative variation of cycles within a predefined dynamic trajectory. According to the present example, the horizontal axis 704 represents time. The vertical axis 702 represents position. Specifically, the vertical axis 702 represents the depth at which the tip of a biopsy needle is positioned at a given point in time. The graph 700 represents varying cycles of a cutting phase.

For example, instead of having the predefined dynamic trajectory follow a similar pattern for each cycle, the cycles can vary such that different motions may be able to cut tissue as desired. Cycles may be varied in multiple ways. In one example, the cycles may vary in depth for a portion 706 of the cutting phase. Specifically, each cycle may extend the needle deeper into the patient's tissue. In some examples, for a portion 708 of the cutting phase, the cycles may involve slower extensions and retractions of the needle.

As described above, in some cases, movement according to a predefined dynamic trajectory may be initiated in response to a user command. In some examples, however, the operator may manually control the motion of the biopsy instrument while the control system adjusts the input to cause the biopsy tool to move according to the predefined dynamic trajectory.

Figure 8:
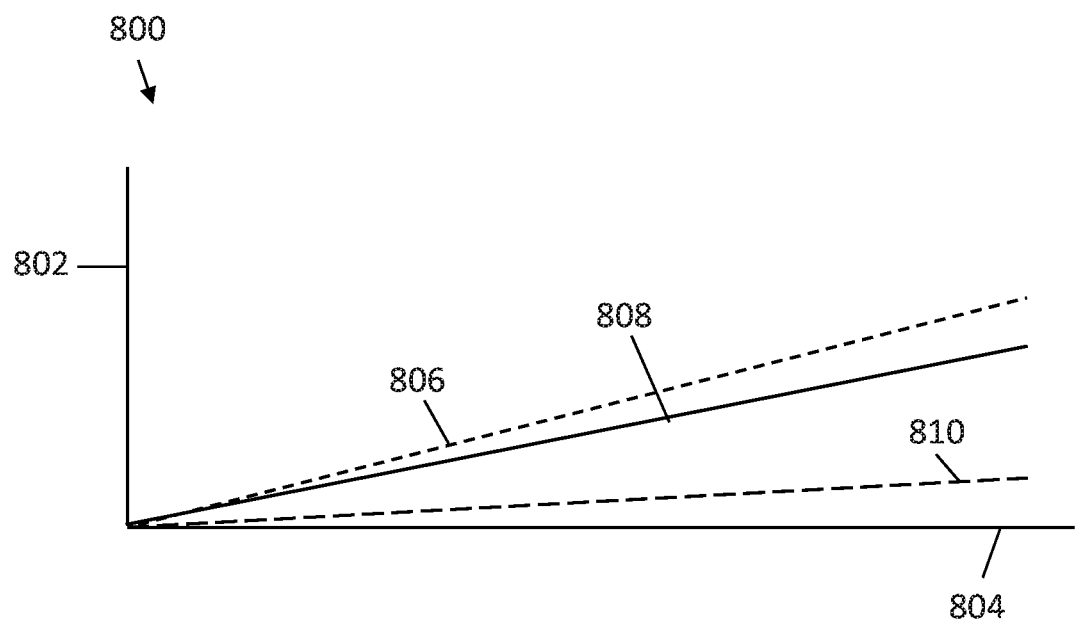
FIG. 8 is a diagram showing an illustrative difference between an input signal to cause a predefined trajectory and a manual input signal, according to one example of principles described herein.

FIG. 8 is a diagram showing an illustrative difference between an input signal to cause a predefined trajectory and a manual input signal. According to the present example, the horizontal axis 804 represents time. The vertical axis 802 represents an input signal, such as electric current that is applied to a motor that actuates a surgical tool in a particular degree of freedom. The input signal is selected to cause the desired movement of the surgical tool so that the position of the tool at specific times is as desired.

Line 808 represents the input signal resulting from manual input from an operator. Line 806 represents the input signal that will cause the surgical tool to move according to the predefined dynamic trajectory. Line 810 represents the difference between the signals represented by lines 806 and 808. Thus, the control system can add the signal represented by line 810 to the manual input signal 808 in order to create an input signal 806 that causes the surgical tool to move according to the predefined trajectory. It is noted that the input signals 806, 808, 810 illustrated in FIG. 8 are used for purposes of discussion and do not necessarily represent an actual input signal that may be used for practical implementation of principles described herein.

Figure 9:
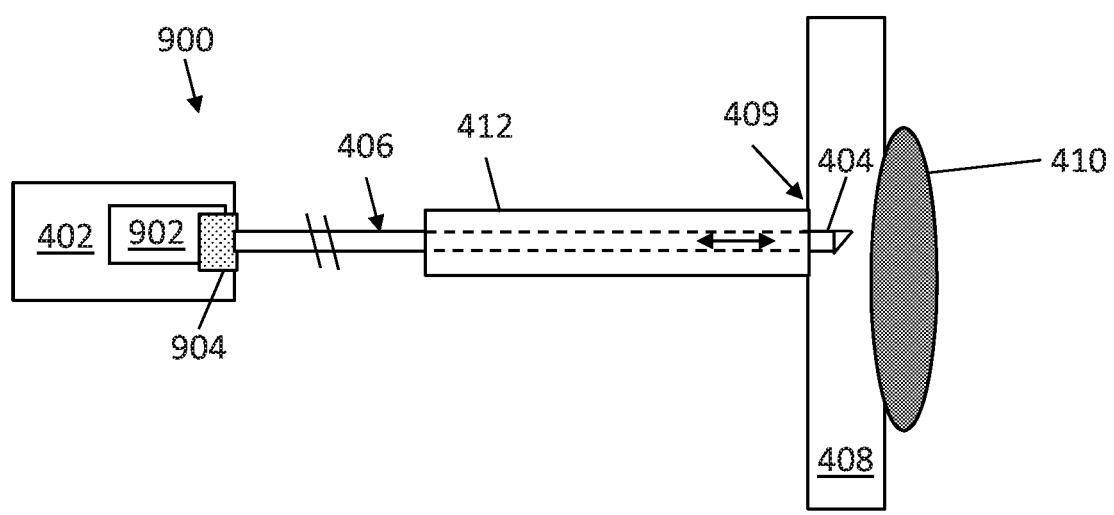
FIG. 9 is a diagram showing an illustrative biopsy tool with a force sensor, according to one example of principles described herein.

FIG. 9 is a diagram showing an illustrative biopsy tool 900 with a force sensing mechanism 904. The force sensing mechanism 904 may allow a control system of the biopsy tool to determine the force experienced by the biopsy needle tip 404. Such information can allow the control system to adjust the input signal to the actuation mechanism 902 to ensure that the biopsy needle tip 404 moves according to the predefined dynamic trajectory. As described above, the input signal is designed to cause the biopsy needle tip 404 to move according to the predefined dynamic trajectory. But, because external factors, such as tougher tissue, may affect the trajectory, the information from the force sensing mechanism 904 can be used to determine how the input signal should be adjusted to cause the acceleration, velocity, position, orientation or other aspect of the motion of the biopsy needle tip 404 to more closely match the predefined dynamic trajectory. According to the present example, a force sensing mechanism 904 is placed at the proximal end of the biopsy instrument 406. According to an alternative embodiment, the force sensor may be positioned distally at or near the biopsy needle tip 404.

In another alternative, the force sensing mechanism 904 may detect a qualitative measure of the contact force at the biopsy needle tip by comparing the difference between the electric current level used to drive the biopsy instrument and an expected current level (e.g., based upon current tissue type, biopsy instrument characteristics, present shape of the catheter guiding the biopsy instrument movement) for the predefined dynamic trajectory. The magnitude by which the actual current level exceeds the expected current level provides an indication of the contact force experienced by the biopsy needle tip. When the tip is experiencing a significant unexpected contact force, more current must be applied to drive the desired dynamic profile.

The force sensing mechanism 902 can be used to estimate the mechanical impedance of the tissue being biopsied. In some cases, such information may help determine if the biopsy needle is within the target location. For example, if the biopsy needle is to pass through some tissue that is not stiff before reaching the target tissue that is expected to be stiff, then it can be known that the biopsy needle 406 is at the proper location for performing the biopsy procedure. In some examples, a local impedance profile is used to qualitatively estimate whether the biopsy needle biopsied through one or more types of tissues. In some examples, if the force sensing mechanism detects a particular force, or, if it is detected that the biopsy instrument is recoiling into the catheter, then the catheter itself may be repositioned such that the tip of the catheter is closer to the wall of the passageway.

Figure 10:
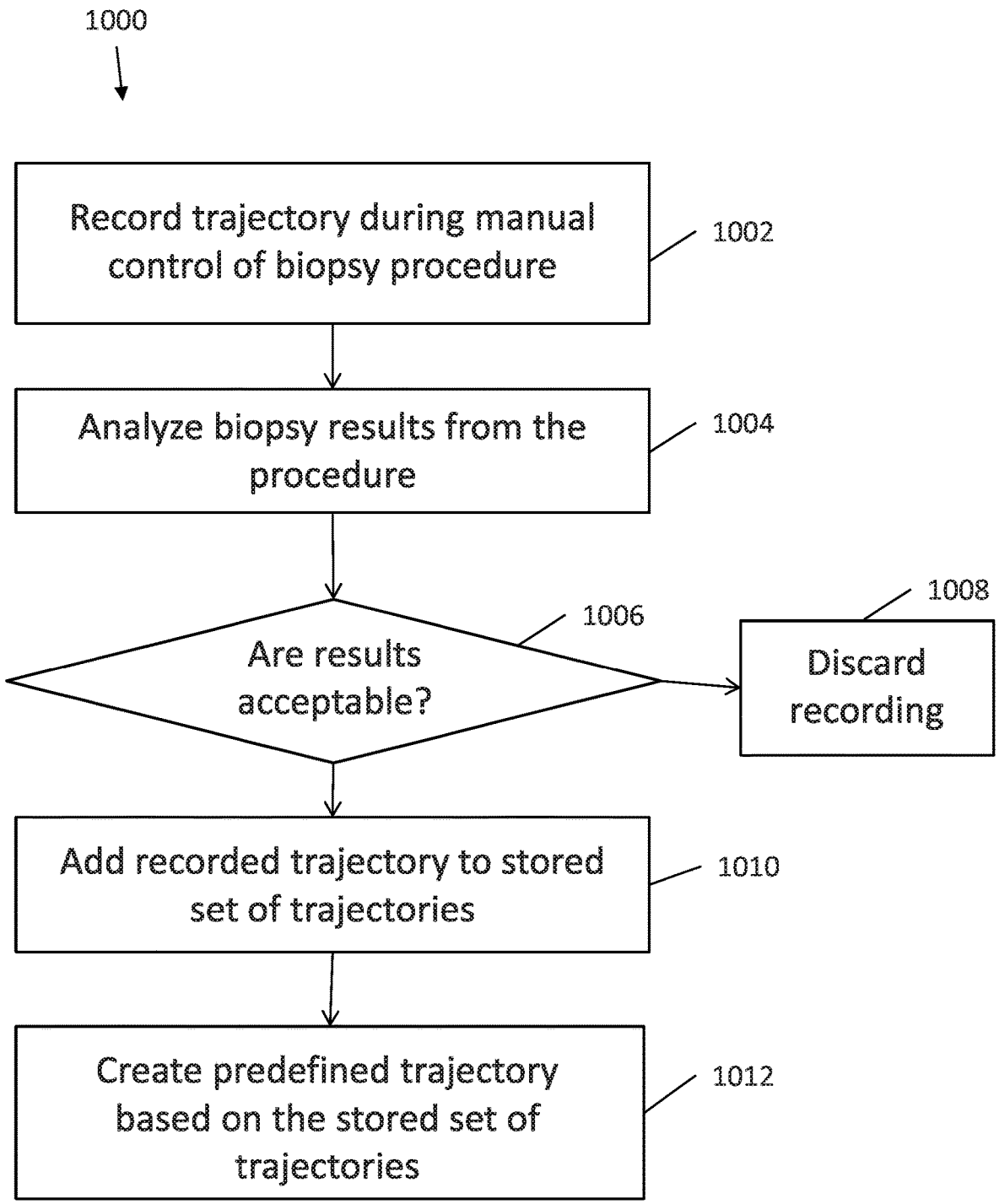
FIG. 10 is a flowchart showing an illustrative method for creating a predefined dynamic trajectory, according to one example of principles described herein.

FIG. 10 is a flowchart showing an illustrative method 1000 for creating a predefined dynamic trajectory. According to the present example, the method 1000 includes a process 1002 for recording an instrument trajectory (including, for example, displacement, velocity, acceleration, orientation, suction action, and obturator removal action) during manual control of a biopsy procedure. In one example, this includes recording the input signal created when an operator uses manual control to manually perform the biopsy procedure. In one example, recording the trajectory includes the use of sensors to monitor the position of the biopsy needle with respect to the biopsy tool carriage to determine the trajectory of the manually controlled biopsy needle. The operator performing the biopsy procedure may be a skilled and experienced clinician so that the biopsy process is performed appropriately.

The method 1000 further includes a process 1004 for analyzing cell samples obtained during the biopsy procedure. This process 1004 may be performed by a separate entity. The cell samples may be assigned a quality metric that indicates how useful they are for an analysis that is helpful in making a diagnostic. If the quality metric is above a particular threshold, then the biopsy procedure used to obtain the cell samples is deemed acceptable. If, however, the assigned quality metric is below the threshold, then the biopsy procedure used to obtain the cell samples is deemed unacceptable.

At process 1006, it is determined whether the biopsy procedure was acceptable. If not, then the recording of the dynamic trajectory for that biopsy procedure can be discarded at process 1008. If, however, the biopsy procedure is deemed acceptable, then the trajectory can be added to a set of stored trajectories at step 1010. The set of stored trajectories includes all the trajectories that are deemed acceptable.

At step 1012, one or more predefined trajectories based on the stored set of trajectories is created. In one example, the final predefined dynamic trajectory may be the recorded trajectory from the stored set of trajectories that is associated with a biopsy procedure that has the highest quality metric assigned to samples obtained from that biopsy procedure. In one example, the predefined dynamic trajectory may be created based on several of the trajectories in the stored set of trajectories. For example, several trajectories may be analyzed for similar components. A composite trajectory may then be created that has components that are similar to the several trajectories. For example, it may be determined that several good trajectories indicate a slow insertion movement and rapid extraction movements. Thus, the composite trajectory would have similar characteristics.

In some examples, the predefined dynamic trajectory can be created from a single recording of a procedure that produced optimum results. Thus, the predefined dynamic trajectory may allow any operator, even an operator without extensive experience and skill, to perform a biopsy and obtain results similar to those of the most effective clinicians.

In some examples, the predefined dynamic trajectory may be created by programming the movement of the biopsy instrument with reference to a recorded trajectories from an actual biopsy operation. For example, it may be determined that certain characteristics of a trajectory result in successful biopsies. Such characteristics may be programmed into the predefined dynamic trajectory.

In some cases, a user may make manual changes to the predefined dynamic trajectory before operation. For example, the user may wish to set a maximum velocity or acceleration. In some cases, the user may wish to alter certain dynamics. This may be because the operator has viewed a scanned image of the target tissue and believes that such modifications will help get a better sample of cells.

Figure 11:
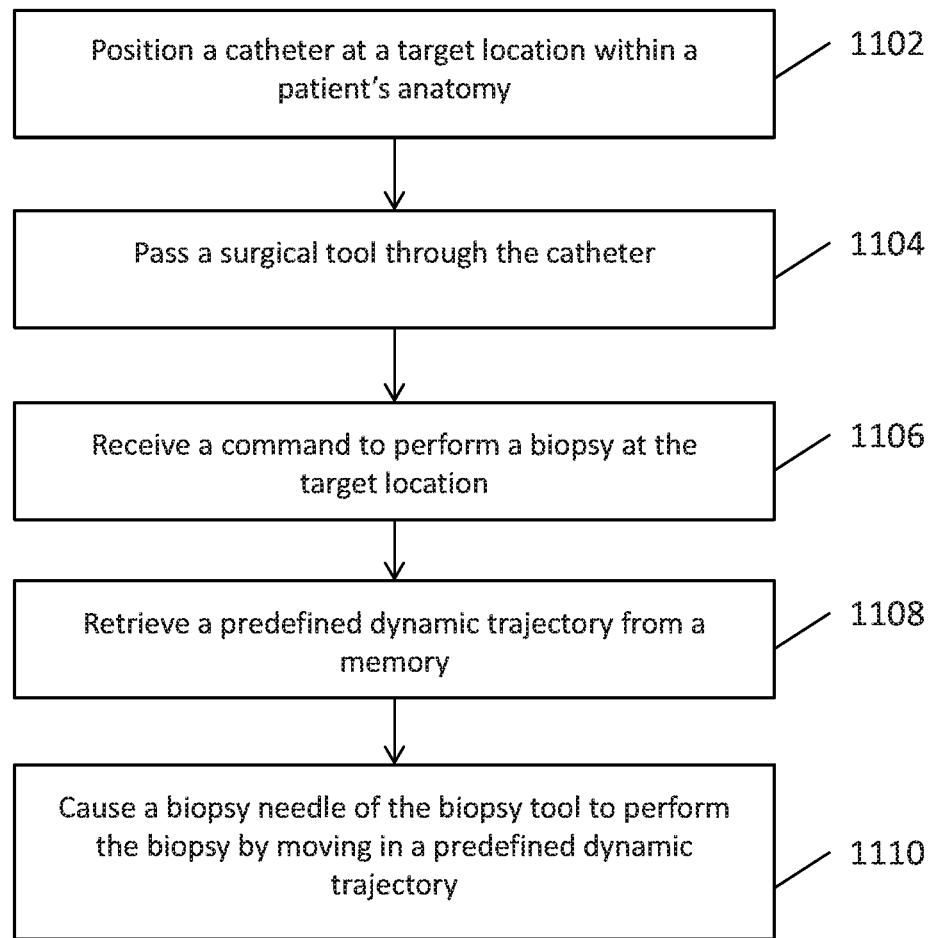
FIG. 11 is a flowchart showing an illustrative method for using a predefined dynamic trajectory for a biopsy instrument, according to one example of principles described herein.

FIG. 11 is a flowchart showing an illustrative method 1100 for using a predefined dynamic trajectory for a biopsy instrument. According to the present example, the method 1100 optionally includes a process 1102 for positioning a catheter at a park location within a patient's anatomy. The catheter includes a working channel that is sized and shaped to receive a surgical tool such as a biopsy tool. The catheter may be steerable such that it can be navigated through a patient's anatomy to arrive at a target location. The park location may be a site from which a surgical operation, such as a biopsy, is to be performed.

The method 1100 further includes a process 1104 for passing a surgical tool through the catheter. Specifically, the surgical tool is inserted into the working channel of the catheter. The surgical tool may be a biopsy tool and include a biopsy needle fixed to the distal end of the tool. Thus, as the biopsy tool moves with respect to the catheter, the needle also moves with respect to the catheter. The surgical tool may be inserted into the catheter before process 1102, during process 1102 or after process 1102.

The method further includes a process 1106 for receiving a command to perform a biopsy from the park location. This command may be received, for example, by a control system in communication with the catheter. The operator may be provided with a control device. After the catheter and biopsy tool are properly placed, the operator can simply engage the control device to cause the biopsy procedure to be performed.

The method further includes a process 1108 for retrieving a predefined dynamic trajectory from a memory device. The predefined dynamic trajectory may be selected by an operator of the biopsy tool. As described above, the predefined dynamic trajectory may be specific to the type of biopsy operation being performed, the type of tissue, the patient condition, or other relevant factors that may affect the desired dynamic trajectory of the biopsy tool.

The method 1100 further includes a process 1110 for causing a biopsy needle of the biopsy tool to perform the biopsy on a target tissue location by moving according to the predefined dynamic trajectory. Thus, in response to the received command, the biopsy instrument moves according to the predefined dynamic trajectory to perform the biopsy procedure. The predefined trajectory may include multiple dynamic control modes, for example a dynamic control mode for an insertion phase and a dynamic control mode for a sampling phase.

The systems and methods of this disclosure may be used for connected bronchial passageways of the lung. The systems and methods may also be suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-surgical applications.

One or more elements in embodiments of the invention may be implemented in software to execute on a processor of a computer system such as control processing system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A biopsy system comprising:
 a biopsy tool comprising a force sensing mechanism configured to sense force received at a distal tip of the biopsy tool; and
 a control system in communication with the biopsy tool, the control system configured to:
  receive a command to perform a biopsy;
  retrieve, from a memory device, a predefined dynamic trajectory for performing the biopsy, wherein the predefined dynamic trajectory includes a plurality of dynamic control modes, wherein each of the plurality of dynamic control modes has a different displacement profile, and wherein at least one different displacement profile comprises a cyclic displacement profile;
  control the biopsy tool to move according to the predefined dynamic trajectory to perform the biopsy; and
  detect, using the force sensing mechanism, a difference between an actual electric current level being used to drive the biopsy toll and an expected electric current level associated with the prededfined dynamic trajectory, wherein the expected electric current level is determined based upon a present shape of the biopsy tool.

2. The biopsy system of claim 1, wherein the plurality of dynamic control modes of the predefined dynamic trajectory comprises a first dynamic control mode for moving the biopsy tool to collect tissue.

3. The biopsy system of claim 2, wherein the plurality of dynamic control modes of the predefined dynamic trajectory comprises a second dynamic control mode for inserting the biopsy tool a predefined distance before initiating the first dynamic control mode.

4. The biopsy system of claim 3, wherein the first dynamic control mode moves the biopsy tool with a predefined first motion profile for a predefined quantity of motion cycles.

5. The biopsy system of claim 4, wherein the second dynamic control mode moves the biopsy tool with a predefined second motion profile, and wherein the predefined first motion profile includes higher tool velocities than the predefined second motion profile.

6. The biopsy system of claim 1, wherein the plurality of dynamic control modes of the predefined dynamic trajectory comprises a suction control mode in which suction is applied to the biopsy tool.

7. The biopsy system of claim 1, further comprising an operator teleoperational control device that initiates the command to perform the biopsy and wherein the control system comprises a teleoperational control system.

8. The biopsy system of claim 1, wherein the predefined dynamic trajectory provides a predefined position for the distal tip of the biopsy tool for a predefined period of time.

9. The biopsy system of claim 1, wherein the predefined dynamic trajectory provides a predefined orientation for the distal tip of the biopsy tool for a predefined period of time.

10. The biopsy system of claim 1, wherein the predefined dynamic trajectory provides a predefined velocity for the distal tip of the biopsy tool for a predefined period of time.

11. The biopsy system of claim 1, wherein the predefined dynamic trajectory provides a predefined acceleration for the distal tip of the biopsy tool for a predefined period of time.

12. The biopsy system of claim 1, further comprising an obturator sized for passage within the biopsy tool and wherein the predefined dynamic trajectory includes an obturator removal mode for removing the obturator from the biopsy tool.

13. The biopsy system of claim 1, wherein the force sensing mechanism is located at a proximal end of the biopsy tool.

14. The biopsy system of claim 1, wherein the force sensing mechanism is located adjacent to the distal tip of the biopsy tool.

15. The biopsy system of claim 1, wherein the control system is configured to adjust the predefined dynamic trajectory based on the force received at the distal tip of the biopsy tool.

16. The biopsy system of claim 1, wherein the control system is further configured to assign a quality metric value to samples obtained by the biopsy tool.

17. The biopsy system of claim 16, wherein the control system is further configured to adjust the predefined dynamic trajectory based on the quality metric value.

18. The biopsy system of claim 1, wherein the control system is further configured to receive a manual input signal from an operator to perform an operator-controlled tissue sampling procedure and wherein the predefined dynamic trajectory includes a dynamic modification mode for modifying the manual input signal to perform a modified operator-controlled tissue sampling procedure.

19. The biopsy system of claim 1 wherein the biopsy tool is an elongated flexible biopsy tool.

20. The biopsy system of claim 19 wherein the control system is further configured to control the elongated flexible biopsy tool to move through an anatomic passageway of a patient anatomy.

21. A biopsy system comprising:
a biopsy tool comprising a force sensing mechanism configured to sense a force received at a distal tip of the biopsy tool; and
a control system in communication with the biopsy tool, the control system configured to:
 receive a command to perform a biopsy;
 retrieve a predefined dynamic trajectory for performing the biopsy from a memory device; and
 control the biopsy tool to move according to the predefined dynamic trajectory to perform the biopsy;
wherein the control system is configured to use the force sensing mechanism to detect a difference between an actual electric current level being used to drive the biopsy tool and an expected electric current level associated with the predefined dynamic trajectory; and
wherein the expected electric current level is determined based upon a present shape of the biopsy tool.

* * * * *